United States Patent [19]
Beck

[11] Patent Number: 5,827,695
[45] Date of Patent: Oct. 27, 1998

[54] DETECTION OF WHEAT FUNGAL PATHOGENS USING THE POLYMERASE CHAIN REACTION

[75] Inventor: James Joseph Beck, Cary, N.C.

[73] Assignee: Novartis Finance Corporation, New York, N.Y.

[21] Appl. No.: 905,314

[22] Filed: Aug. 1, 1997

[51] Int. Cl.$^6$ ............... C12P 19/34; C12Q 1/68; C07H 21/04

[52] U.S. Cl. ............ 435/91.2; 435/6; 435/91.51; 536/24.32; 536/24.33; 935/8; 935/9; 935/77; 935/78

[58] Field of Search ............... 435/6, 91.2, 91.1, 435/91.5, 91.51; 536/231, 23.7, 24.1, 24.32, 24.33; 935/6, 8, 9, 17, 77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,585,238 | 12/1996 | Ligon et al. | 435/6 |
| 5,707,802 | 1/1998 | Sandhu et al. | 435/6 |

FOREIGN PATENT DOCUMENTS

| | | |
|---|---|---|
| WO 91/14001 | 9/1991 | WIPO . |
| WO95/29260 | 11/1995 | WIPO . |

OTHER PUBLICATIONS

Hering et al. Zvechtungsforschung 1(2):328–331, 1995.

O'Donnell et al. Molecular Phylogenetics and Evolution 7:103–116, Feb. 1997.

Bateman et al., "Relationships Among Fusarium SPP. Estimated by Comparing Restriction Fragment Length Polymorphisms in Polymerase Chain Reaction–Amplified Ribosomal DNA", *Cereal Research Communication*, 25(3/2):577–578 (1997).

Nicholson et al., "Detection and Quantification of Individual Fungal Species in Fusarium Disease Complexes of Cereals by Polymerase Chain Reaction (PCR)", *Cereal Research Communications*, 23(3/1):477–482 (1997).

Nicholson et al., "Restriction fragment length polymorphism analysis of variation in Fusarium species causing ear blight of cereals", *Plant Pathology* 42:905–914 (1993).

Nicholson et al., "Development of a PCR assay to identify and quantify *Microdochium nivale* var. *nivale* and *Microdochium nivale* var. *majus* in wheat", *Physiological and Molecular Plant Pathology*, 48: 257–271 (1996).

Parry et al., "Development of a PCR assay to detect *Fusarium poae* in wheat", *Plant Pathology*, 45: 383–391 (1996).

Parry et al., "Analysis of *Microdochium nivale* Isolates from wheat in the UK during 1993", *Ann. Appl. Biol.*, 126:449–455 (1995).

Schesser et al., "Use of Polymerase Chain Reaction To Detect the Take–All Fungus, *Gaeumannomyces graminis*, in Infected Wheat Plats", *Applied and Environ. Microbiol.*, 57(2):553–556 (1991).

Schilling et al., "Polymerase Chain Reaction–Based Assays for Species–Specific Detection of *Fusarium culmorum*, *F. graminearum*, and *F. avenaceum*", *Phytopathology*, 86(5):515–527 (1996).

Stratagene Catalog, 1988, p. 39.

Tisserat et al., "Selective Amplification of rDNA Internal Transcribed Spacer Regions to Detect *Ophiosphaerella korrae* and *O. herpotricha*", *Phytopathology*, 84(5): 478–482 (1994).

White, T.J., et al., "Amplification and Direct Sequencing of Fungal Ribosomal RNA Genes for Phylogenetics", In: *PCR Protocols*; Academic Press Inc., pp. 315–322 (1990).

Xue et al., "Pathotype identification of *Leptosphaeria maculans* with PCR and oligonucleotide primrers from ribosomal internal transribed spacer sequences", *Physiological and Molecular Plant Pathology*, 41: 179–188 (1992).

GenBank Accession No. UO4237, computer printout, Jan. 3, 1994.

*Primary Examiner*—W. Gary Jones
*Assistant Examiner*—Debra Shoemaker
*Attorney, Agent, or Firm*—J. Timothy Meigs

[57] ABSTRACT

Internal Transcribed Spacer (ITS) DNA sequences from the ribosomal RNA gene region are described for different species and strains of wheat fungal pathogens, including *Fusarium* spp. and *Microdochium nivale*. Specific primers from within these sequences are identified as being useful for the identification of the fungal isolates using PCR-based techniques.

21 Claims, 3 Drawing Sheets

```
                        10         20         30         40         50         60
                         |          |          |          |          |          |
Fave.con       TCCGTAGGTGAACCTGCGGAGGGATCATTACCGAGTTTAC~AACTCCCAAACCCCTGTGA      59
Fculm.con      ~~~~~~~~~~~~~~~~~~~~GAGGGATCATTACCGAGTTTACTRACTCCCAAACCCCTGTGA      42
Fgram.con      ~~~~~~~~~~~~~~~~~~~~~~GGATCATTACCGAGTTTACWSACTCCCAAACCCCTGTGA      39
Fpoae.con      TCCGTAGGTGAACCTGCGGAGGGATCATTACCGAGTTTAC~AACTCCCAAACCCCTGTGA      59
Mniv.con       TCCGTAGGTGAACCTGCGGAGGGATCATTACTGAGTTT~TTAACTCTCCAAACCATGTGA      59
PCRFmon1.con   TCCGTAGGTGAACCTGCGGAGGGATCATTACCGAGTTTAC~AACTCCCAAACCCCTGTGA      59

70         80         90        100        110        120
                        |          |          |          |          |          |
Fave.con       ACATACCTTAATGTTGCCTCGGCGGATCAGCCCGCCCYGTAAACGGACGGCCCGCC         119
Fculm.con      ACDTACCTT~ATGTTGCCTCGGCGGATCAGCCCGCCCCGTAAAAAGGACGGCCCGCC        101
Fgram.con      ACATACCTT~ATGTTGCCTCGGCGGATCAGCCCGCCCCG~~~AAAGGACGGCCCGCC         95
Fpoae.con      ACATACCWTTATGTTGCCTCGGCGGATCAGCCCGCCKCCYYGTAAAACGGACGGCCCGCC     119
Mniv.con       ACTTACCAC~~TGTTGCCTCGGTGAT~GGTGC~TGTCTCTCGGGACGGTRCCACC~GCC      114
PCRFmon1.con   ACATACCTT~ATGTTGCCTCGGCGGATCAGCCCGCCCCGTAAAAAGGGACGGCCCGCC       118

130        140        150        160        170        180
                        |          |          |          |          |          |
Fave.con       AGAGGA~~~CCCAAACTCTAATGTTTCTTATTGTAACTTCTGAGTAAAACAAACAAATAA    176
Fculm.con      GCAGGAA~CCCTAAACTCTG~~~~TTTTTAGTGGAACTTCTGAGTATAAAAAACAAATAA    156
Fgram.con      GCAGGAA~CCCTAAACTCTG~~~~TTTTTAGTGGAACTTCTGAGTATAAAAAACAAATAA    150
Fpoae.con      GCAGGAAACCCTAAACTCTG~~~~TTTTTAGTGGAACTTCTGAGTATAAAAAACAAATAA    175
Mniv.con       GGTGGACTACCTAAACTCTGTTGTTAATTTTTGYCAA~~~~TCTGAATCAAACTAAGAAATAA  170
PCRFmon1.con   GCAGGAA~CCCTAAACTCTG~~~~TTTTTAGTGGAACTTCTGAGTATAAAAAACAAATAA    173

190        200        210        220        230        240
                        |          |          |          |          |          |
Fave.con       ATCAAAACTTTCAACAACGGATCTCTTGGTTCTCGGCATCGATGAAGAACGCAGCAAAATG   236
Fculm.con      ATCAAAACTTTCAACAACGGATCTCTTGGTTCTCGGCATCGATGAAGAACGCAGCAAAATG   216
Fgram.con      ATCAAAACTTTCAACAACGGATCTCTTGGTTCTCGGCATCGATGAAGAACGCAGCASCRAAATG 210
Fpoae.con      ATCAAAACTTTCAACAACGGATCTCTTGGTTCTCGGCATCGATGAAGAACGCAGCAAAATG   235
Mniv.con       GTTAAAACTTTCAACAACGGATCTCTTGGTTCTTGGCATCGATGAAGAACGCAGCGAAATG   230
PCRFmon1.con   ATCAAAACTTTCAACAACGGATCTCTTGGTTTCTGGCATCGATGAAGAACGCAGCAAATAA   233
```

FIGURE 1A

```
                         250       260       270       280       290       300
                         |         |         |         |         |         |
Fave.con       CGATAAGTAATGTGAATTGCAGAATTCAGTGAATCATCATGAATCTTTGAACGCACATTGCG 296
Fculm.con      CGATAAGTAATGTGAATTGCAGAATTCAGTGAATCATCAGAATCTTTGAACGCACATTGCG 276
Fgram.con      CGATAAGTAATGTGWATTGCAGAATTCAGTGAATCATGAAWCGAATCTTTGAACGCWSATTGCK 270
Fpoae.con      CGATAAGTAATGTGAATTGCAGAATTCAGTGAATCATCGAATCTTTGAACGCACATTGCG 295
Mniv.con       CGATAAGTAATGTGAATTGCAGAATTCAGTGAATCATCGAATCTTTGAACGCACATTGCG 290
PCRFmon1.con   CGATAAGTAATGTGAATTGCAGAATTCAGTGAATCATCGAATCTTTG

```
                  490        500        510        520        530        540
                   |          |          |          |          |          |
Fave.con      CGG~CCATGCCGTAAAACCCCAACTTCTGAATGTTGACCTCGGATCAGGTAGGAATACCCC  530
Fculm.con     CGG~CYACGCCGTTAAACCCCAACTTCTGAATGTTGACCTCGGATCAGGTAGGAATACCCC  498
Fgram.con     CGG~CTACGCCGTTAAACCCCAACTTCTGAATGTTGACCTCGGATCAGGTAGGAATACCCC  492
Fpoae.con     CGG~CCACGCCGTTAAACCCCAACTTCTGAATGTTGACCTCGGATCAGGTAGGAATACCCC  516
Mniv.con      TAAACCGCACCCTTCGGGGCACTTTTTAATGTTGACCTCGGATCAGGTAGGAATACCCC    525
PCRFmon1.con  CGG~CCACGCCGTTAAACCCCAACTTCTGAATGTTGACCTCGGATCAGGTAGGAATACCCC  514

5,827,695

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer ITS1"

( x i ) SEQUENCE DESCRIPTION: SEQ ID NO:1:

TCCGTAGGTG AACCTGCGG                       19

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer ITS2"

( x i ) SEQUENCE DESCRIPTION: SEQ ID NO:2:

GCTGCGTTCT TCATCGATGC                      20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer ITS3"

( x i ) SEQUENCE DESCRIPTION: SEQ ID NO:3:

GCATCGATGA AGAACGCAGC                      20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer ITS4"

( x i ) SEQUENCE DESCRIPTION: SEQ ID NO:4:

TCCTCCGCTT ATTGATATGC                      20

( 2 ) INFORMATION FOR SEQ ID NO:5:

( i ) SEQUENCE CHARACTERISTICS:
        ( A ) LENGTH: 17 base pairs
        ( B ) TYPE: nucleic acid ( C ) STRANDEDNESS: single
            ( D ) TOPOLOGY: linear ( i i ) MOLECULE TYPE: other nucleic acid
            ( A ) DESCRIPTION: /desc = "M13 Universal-20 Primer"

( x i ) SEQUENCE DESCRIPTION: SEQ ID NO:5:

GTAAAACGAC GGCCAGT                                                                                    17

( 2 ) INFORMATION FOR SEQ ID NO:6:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "Reverse Primer used in
                    Example 2"

( x i ) SEQUENCE DESCRIPTION: SEQ ID NO:6:

AACAGCTATG ACCATG                                                                                     16

( 2 ) INFORMATION FOR SEQ ID NO:7:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer JB605"

( x i ) SEQUENCE DESCRIPTION: SEQ ID NO:7:

CCAAACCATG TGAACTTACC                                                                                 20

( 2 ) INFORMATION FOR SEQ ID NO:8:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer JB606"

( x i ) SEQUENCE DESCRIPTION: SEQ ID NO:8:

GGACTACCTA AACTCTGTT                                                                                  19

( 2 ) INFORMATION FOR SEQ ID NO:9:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "primer JB607"

( x i ) SEQUENCE DESCRIPTION: SEQ ID NO:9:

AGGGATCATT ACCGAGTTT                                                                                  19

( 2 ) INFORMATION FOR SEQ ID NO:10:

( i ) SEQUENCE CHARACTERISTICS:
            ( A ) LENGTH: 19 base pairs ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "primer JB609"

( x i ) SEQUENCE DESCRIPTION: SEQ ID NO:10:

TCCGGCTTGC AGAAGCGAG                                                                                19

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "primer JB610"

( x i ) SEQUENCE DESCRIPTION: SEQ ID NO:11:

GAAGGGTGCG GTTTATGGCT                                                                               20

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "primer JB611"

( x i ) SEQUENCE DESCRIPTION: SEQ ID NO:12:

GCCACCGCCG GTGGAC                                                                                   16

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "primer JB612"

( x i ) SEQUENCE DESCRIPTION: SEQ ID NO:13:

GGTGCTGTCT CTCGGGAC                                                                                 18

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "primer JB613"

( x i ) SEQUENCE DESCRIPTION: SEQ ID NO:14:

AGTCAATCTG AATCAAACTA AG                                                                            22

( 2 ) INFORMATION FOR SEQ ID NO:15:

( i ) SEQUENCE CHARACTERISTICS:
        ( A ) LENGTH: 24 base pairs (B) TYPE: nucleic acid
            (C) STRANDEDNESS: single
            (D) TOPOLOGY: linear (i i) MOLECULE TYPE: other nucleic acid
            (A) DESCRIPTION: /desc = "primer JB614"

(x i) SEQUENCE DESCRIPTION: SEQ ID NO:15:

CTAAACTCTG TTAATTTTTG TCAA 24

(2) INFORMATION FOR SEQ ID NO:16:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "primer JB578"

(x i) SEQUENCE DESCRIPTION: SEQ ID NO:16:

CCGCGACGAT TACCAG 16

(2) INFORMATION FOR SEQ ID NO:17:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "primer JB571"

(x i) SEQUENCE DESCRIPTION: SEQ ID NO:17:

TAACGATATG TAAATTACTA CGCT 24

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (i i) MOLECULE TYPE: other nucleic acid
            (A) DESCRIPTION: /desc = "primer JB572"

(x i) SEQUENCE DESCRIPTION: SEQ ID NO:18:

AAGTTGGGGT TTAACGGC 18

(2) INFORMATION FOR SEQ ID NO:19:

(i) SEQUENCE CHARACTERISTICS:
            (A) LENGTH: 504 base pairs
            (B) TYPE: nucleic acid
            (C) STRANDEDNESS: single
            (D) TOPOLOGY: linear (i i) MOLECULE TYPE: DNA (genomic)

(v i) ORIGINAL SOURCE:
            (A) ORGANISM: Fusarium culmorum
            (C) INDIVIDUAL ISOLATE: R-5106, R- 5126, and R-5146
                    (consensus sequence)

(i x) FEATURE:
            (A) NAME/KEY: misc_feature
            (B) LOCATION: 1..12
            (D) OTHER INFORMATION: /note= "3'end of small subunit
                    rRNA gene"

( i x ) FEATURE:
  ( A ) NAME/KEY: misc_feature
  ( B ) LOCATION: 13..161
  ( D ) OTHER INFORMATION: /note= "ITS 1"

( i x ) FEATURE:
  ( A ) NAME/KEY: misc_feature
  ( B ) LOCATION: 162..318
  ( D ) OTHER INFORMATION: /note= "5.8S rRNA gene"

( i x ) FEATURE:
  ( A ) NAME/KEY: misc_feature
  ( B ) LOCATION: 319..472
  ( D ) OTHER INFORMATION: /note= "ITS 2"

( i x ) FEATURE:
  ( A ) NAME/KEY: misc_feature
  ( B ) LOCATION: 473..504
  ( D ) OTHER INFORMATION: /note= "5'end of large subunit
    rRNA gene"

( x i ) SEQUENCE DESCRIPTION: SEQ ID NO:19:

```
GAGGGATCAT TACCGAGTTT ACTRACTCCC AAACCCCTGT GAACDTACCT TATGTTGCCT      60
CGGCGGATCA GCCCGCGCCC CGTAAAAAGG GACGGCCCGC CGCAGGAACC CTAAACTCTG     120
TTTTTAGTGG AACTTCTGAG TATAAAAAAC AAATAAATCA AAACTTTCAA CAACGGATCT     180
CTTGGTTCTG GCATCGATGA AGAACGCAGC AAAATGCGAT AAGTAATGTG AATTGCAGAA     240
TTCAGTGAAT CATCGAATCT TTGAACGCAC ATTGCGCCCG CCAGTATTCT GGCGGGCATG     300
CCTGTTCGAG CGTCATTTCA ACCCTCAAGC CAGCTTGGT  GTTGGGAGCT GCAGTCCTGC     360
TGCACTCCCC AAATACATTG GCGGTCACGT CGRAGCTTCC ATAGCGTAGT AATTTACATA     420
TCGTTACTGG TAATCGTCGC GGCYACGCCG TTAAACCCCA ACTTCTGAAT GTTGACCTCG     480
GATCAGGTAG GAATACCCGC TGAA                                            504
```

( 2 ) INFORMATION FOR SEQ ID NO:20:

( i ) SEQUENCE CHARACTERISTICS:
    ( A ) LENGTH: 503 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Fusarium graminearum
    ( C ) INDIVIDUAL ISOLATE: R-8417, R- 8422, and R-8546
      ( c o n s e n s u s  s e q u e n c e )

( i x ) FEATURE:
    ( A ) NAME/KEY: misc_feature
    ( B ) LOCATION: 1..9
    ( D ) OTHER INFORMATION: /note= "3'end of small subunit
      rRNA gene"

( i x ) FEATURE:
    ( A ) NAME/KEY: misc_feature
    ( B ) LOCATION: 10..155
    ( D ) OTHER INFORMATION: /note= "ITS 1"

( i x ) FEATURE:
    ( A ) NAME/KEY: misc_feature
    ( B ) LOCATION: 156..312
    ( D ) OTHER INFORMATION: /note= "5.8S rRNA gene"

( i x ) FEATURE:
    ( A ) NAME/KEY: misc_feature
    ( B ) LOCATION: 313..466
    ( D ) OTHER INFORMATION: /note= "ITS 2"

( i x ) FEATURE:

(A) NAME/KEY: misc_feature
(B) LOCATION: 467..503
(D) OTHER INFORMATION: /note= "5'end of large subunit rRNA gene"

(xi) SEQUENCE DESCRIPTION: SEQ ID NO:20:

| | | | | | |
|---|---|---|---|---|---|
| GGATCATTAC | CGAGTTTACW | SACTCCCAAA | CCCCTGTGAA | CATACCTTAT | GTTGCCTCGG | 60
| CGGATCAGCC | CGCGCCCCGA | AAGGGACGGC | CCGCCGCAGG | AACCCTAAAC | TCTGTTTTTA | 120
| GTGGAACTTC | TGAGTATAAA | AAACAAATAA | ATCAAAACTT | TCAACAACGG | ATCTCTTGGT | 180
| KCTGGCATCG | ATGAAGAACG | CASCRAAATG | CGATAAGTAA | TGTGWATTGC | AGAATTCAGT | 240
| GAATCAWCGA | ATCTTTGAAC | GCWSATTGCK | MCCRCCAGTA | TTCTGGCGGG | CATGCCTGTT | 300
| CGAGCGTCAT | TTCAACCCTC | AAGCCCAGVT | TGGTGTKGGG | GARYTGCAGK | CCTRYTKCAC | 360
| TCCCCAAATA | ARTTGGCGGT | CACGTCGAAC | TTCCATAGCG | TAGTAAGTTA | CACATCGTTA | 420
| CTGGTAATCG | TCGCGGCTAC | GCCGTTAAAC | CCCAACTTCT | GAATGTTGAC | CTCGGATCAG | 480
| GTAGGAATAC | CCGCTGAAGG | TAA | | | | 503

(2) INFORMATION FOR SEQ ID NO:21:

(i) SEQUENCE CHARACTERISTICS:
    (A) LENGTH: 545 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Fusarium moniliforme
    (C) INDIVIDUAL ISOLATE: 4551

(vii) IMMEDIATE SOURCE:
    (B) CLONE: pCRFMON1

(ix) FEATURE:
    (A) NAME/KEY: misc_feature
    (B) LOCATION: 1..30
    (D) OTHER INFORMATION: /note= "3'end of small subunit rRNA gene"

(ix) FEATURE:
    (A) NAME/KEY: misc_feature
    (B) LOCATION: 31..178
    (D) OTHER INFORMATION: /note= "ITS 1"

(ix) FEATURE:
    (A) NAME/KEY: misc_feature
    (B) LOCATION: 179..335
    (D) OTHER INFORMATION: /note= "5.8S rRNA gene"

(ix) FEATURE:
    (A) NAME/KEY: misc_feature
    (B) LOCATION: 336..488
    (D) OTHER INFORMATION: /note= "ITS 2"

(ix) FEATURE:
    (A) NAME/KEY: misc_feature
    (B) LOCATION: 489..545
    (D) OTHER INFORMATION: /note= "5'end of large subunit rRNA gene"

(xi) SEQUENCE DESCRIPTION: SEQ ID NO:21:

| | | | | | |
|---|---|---|---|---|---|
| TCCGTAGGTG | AACCTGCGGA | GGGATCATTA | CCGAGTTTAC | AACTCCCAAA | CCCCTGTGAA | 60
| CATACCTTAT | GTTGCCTCGG | CGGATCAGCC | CGCGCCCCGT | AAAAGGGAC | GGCCCGCCGC | 120
| AGGAACCCTA | AACTCTGTTT | TTAGTGGAAC | TTCTGAGTAT | AAAAACAAA | TAAATCAAAA | 180
| CTTTCAACAA | CGGATCTCTT | GGTTCTGGCA | TCGATGAAGA | ACGCAGCAAA | ATGCGATAAG | 240

```
TAATGTGAAT  TGCAGAATTC  AGTGAATCAT  CGAATCTTTG  AACGCACATT  GCGCCCGCCA    300

GTATTCTGGC  GGGCATGCCT  GTTCGAGCGT  CATTTCAACC  CTCAAGCCCA  GCTTGGTGTT    360

GGGAGCTGCA  GTCCTGCTGC  ACTCCCCAAA  TACATTGGCG  GTCACGTCGA  GCTTCCATAG    420

CGTAGTAATT  TACACATCGT  TACTGGTAAT  CGTCGCGGCC  ACGCCGTTAA  ACCCCAACTT    480

CTGAATGTTG  ACCTCGGATC  AGGTAGGAAT  ACCCGCTGAA  CTTAAGCATA  TCAATAAGCG    540

GAGGA                                                                    545
```

(2) INFORMATION FOR SEQ ID NO:22:

(i) SEQUENCE CHARACTERISTICS:
        (A) LENGTH: 546 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Fusarium poae
        (C) INDIVIDUAL ISOLATE: T-427, T-534, and T-756 (consensus
            sequence)

(vii) IMMEDIATE SOURCE:
        (B) CLONE: pCRFpoaeT427(1-2), pCRFpoaeT534(2-2), and
            pCRFpoaeT756(3-1)

(ix) FEATURE:
        (A) NAME/KEY: misc_feature
        (B) LOCATION: 1..30
        (D) OTHER INFORMATION: /note= "3'end of small subunit
            rRNA gene"

(ix) FEATURE:
        (A) NAME/KEY: misc_feature
        (B) LOCATION: 31..180
        (D) OTHER INFORMATION: /note= "ITS 1"

(ix) FEATURE:
        (A) NAME/KEY: misc_feature
        (B) LOCATION: 181..337
        (D) OTHER INFORMATION: /note= "5.8S rRNA gene"

(ix) FEATURE:
        (A) NAME/KEY: misc_feature
        (B) LOCATION: 338..489
        (D) OTHER INFORMATION: /note= "ITS 2"

(ix) FEATURE:
        (A) NAME/KEY: misc_feature
        (B) LOCATION: 490..546
        (D) OTHER INFORMATION: /note= "5'end of large subunit
            rRNA gene"

(xi) SEQUENCE DESCRIPTION: SEQ ID NO:22:

```
TCCGTAGGTG  AACCTGCGGA  GGGATCATTA  CCGAGTTTAC  AACTCCCAAA  CCCCTGTGAA     60

CATACCTTTA  TGTTGCCTCG  GCGGATCAGC  CCGCGCCCCG  TAAAACGGGA  CGGCCCGCCG    120

CAGGAAACCC  TAAACTCTGT  TTTTAGTGGA  ACTTCTGAGT  ATAAAAACA   AATAAATCAA    180

AACTTTCAAC  AACGGATCTC  TTGGTTCTGG  CATCGATGAA  GAACGCAGCA  AAATGCGATA    240

AGTAATGTGA  ATTGCAGAAT  TCAGTGAATC  ATCGAATCTT  TGAACGCACA  TTGCGCCCGC    300

CAGTATTCTG  GCGGGCATGC  CTGTTCGAGC  GTCATTTCAA  CCCTCAAGCC  CAGCTTGGTG    360

TTGGGATCTG  TGTGCAAACA  CAGTCCCCAA  ATTGATTGGC  GGTCACGTCG  AGCTTCCATA    420

GCGTAGTAAT  TTACACATCG  TTACTGGTAA  TCGTCGCGGC  CACGCCGTTA  AACCCCAACT    480

TCTGAATGTT  GACCTCGGAT  CAGGTAGGAA  TACCCGCTGA  ACTTAAGCAT  ATCAATAAGC    540

GGAGGA                                                                   546
```

( 2 ) INFORMATION FOR SEQ ID NO:23:

( i ) SEQUENCE CHARACTERISTICS:
        ( A ) LENGTH: 556 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Microdochium nivale
        ( C ) INDIVIDUAL ISOLATE: 72, 520, and 18222 (consensus
              sequence)

( v i i ) IMMEDIATE SOURCE:
        ( B ) CLONE: pCRMniv72(5-2), pCRMniv520(4-2), and
              pCRMniv18222(6-2)

( i x ) FEATURE:
        ( A ) NAME/KEY: misc_feature
        ( B ) LOCATION: 1..30
        ( D ) OTHER INFORMATION: /note= "3'end of small subunit
              rRNA gene"

( i x ) FEATURE:
        ( A ) NAME/KEY: misc_feature
        ( B ) LOCATION: 31..175
        ( D ) OTHER INFORMATION: /note= "ITS 1"

( i x ) FEATURE:
        ( A ) NAME/KEY: misc_feature
        ( B ) LOCATION: 176..332
        ( D ) OTHER INFORMATION: /note= "5.8S rRNA gene"

( i x ) FEATURE:
        ( A ) NAME/KEY: misc_feature
        ( B ) LOCATION: 333..499
        ( D ) OTHER INFORMATION: /note= "ITS 2"

( i x ) FEATURE:
        ( A ) NAME/KEY: misc_feature
        ( B ) LOCATION: 500..556
        ( D ) OTHER INFORMATION: /note= "5'end of large subunit
              rRNA gene"

( x i ) SEQUENCE DESCRIPTION: SEQ ID NO:23:

```
TCCGTAGGTG  AACCTGCGGA  GGGATCATTA  CTGAGTTTTT  AACTCTCCAA  ACCATGTGAA    60
CTTACCACTG  TTGCCTCGGT  GGATGGTGCT  GTCTCTCGGG  ACGGTGCCAC  CGCCGGTGGA   120
CTACCTAAAC  TCTGTTAATT  TTTGTCAATC  TGAATCAAAC  TAAGAAATAA  GTTAAAACTT   180
TCAACAACGG  ATCTCTTGGT  TCTGGCATCG  ATGAAGAACG  CAGCGAAATG  CGATAAGTAA   240
TGTGAATTGC  AGAATTCAGT  GAATCATCGA  ATCTTTGAAC  GCACATTGCG  CCCATTAGTA   300
TTCTAGTGGG  CATGCCTGTT  CGAGCGTCAT  TTCAACCCTT  AAGCCTAGCT  TAGTGTTGGG   360
AGACTGCCTA  ATACGCAGCT  CCTCAAAACC  AGTGGCGGAG  TCGGTTCGTG  CTCTGAGCGT   420
AGTAATTTTT  TATCTCGCTT  CTGCAAGCCG  GACTGGCAAC  AGCCATAAAC  CGCACCCTTC   480
GGGGGCACTT  TTTAATGGTT  GACCTCGGAT  CAGGTAGGAA  TACCCGCTGA  ACTTAAGCAT   540
ATCAATAAGC  GGAGGA                                                      556
```

( 2 ) INFORMATION FOR SEQ ID NO:24:

( i ) SEQUENCE CHARACTERISTICS:
        ( A ) LENGTH: 561 base pairs
        ( B ) TYPE: nucleic acid
        ( C ) STRANDEDNESS: single
        ( D ) TOPOLOGY: linear ( i i ) MOLECULE TYPE: DNA (genomic)

(v i) ORIGINAL SOURCE:
    (B) STRAIN: Fusarium avenaceum
    (C) INDIVIDUAL ISOLATE: 64452 and R- 4045 (consensus sequence)

(i x) FEATURE:
    (A) NAME/KEY: misc_feature
    (B) LOCATION: 1..30
    (D) OTHER INFORMATION: /note= "3'end of small subunit rRNA gene"

(i x) FEATURE:
    (A) NAME/KEY: misc_feature
    (B) LOCATION: 31..181
    (D) OTHER INFORMATION: /note= "ITS 1"

(i x) FEATURE:
    (A) NAME/KEY: misc_feature
    (B) LOCATION: 182..338
    (D) OTHER INFORMATION: /note= "5.8S rRNA gene"

(i x) FEATURE:
    (A) NAME/KEY: misc_feature
    (B) LOCATION: 339..504
    (D) OTHER INFORMATION: /note= "ITS 2"

(i x) FEATURE:
    (A) NAME/KEY: misc_feature
    (B) LOCATION: 505..561
    (D) OTHER INFORMATION: /note= "5'end of large subunit rRNA gene"

(x i) SEQUENCE DESCRIPTION: SEQ ID NO:24:

| | | | | | | |
|---|---|---|---|---|---|---|
| TCCGTAGGTG | AACCTGCGGA | GGGATCATTA | CCGAGTTTAC | AACTCCCAAA | CCCCTGTGAA | 60 |
| CATACCTTAA | TGTTGCCTCG | GCGGATCAGC | CCGCGCCCYG | TAAAACGGGA | CGGCCCGCCA | 120 |
| GAGGACCCAA | ACTCTAATGT | TTCTTATTGT | AACTTCTGAG | TAAAACAAAC | AAATAAATCA | 180 |
| AAACTTTCAA | CAACGGATCT | CTTGGTTCTG | GCATCGATGA | AGAACGCAGC | AAAATGCGAT | 240 |
| AAGTAATGTG | AATTGCAGAA | TTCAGTGAAT | CATCGAATCT | TTGAACGCAC | ATTGCGCCCG | 300 |
| CTGGTATTCC | GGCGGGCATG | CCTGTTCGAG | CGTCATTTCA | ACCCTCAAGC | CCCCGGGTTT | 360 |
| GGTGTTGGGG | ATCGGCTCTG | CCTTMYGGCG | GTGCCGCCCC | CGAAATACAT | TGGCGGTCTC | 420 |
| GCTGCAGCCT | CCATTGCGTA | GTAGCTAACA | CCTCGCAACT | GGAACGCGGC | GCGGCCATGC | 480 |
| CGTAAAACCC | CAACTTCTGA | ATGTTGACCT | CGGATCAGGT | AGGAATACCC | GCTGAACTTA | 540 |
| AGCATATCAA | TAAGCGGAGG | A | | | | 561 |

DETECTION OF WHEAT FUNGAL PATHOGENS USING THE POLYMERASE CHAIN REACTION

FIELD OF THE INVENTION

The present invention relates to the use of species-specific primers in polymerase chain reaction assays for the detection of fungal pathogens of wheat. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; Seed Sci. & Technol. 9:679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; Proc. 1981 Brit. Crop Prot. Conf.) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and Mycosphaerella fijiensis to triazoles to mention just a few (Jones and Clifford; Cereal Diseases, John Wiley, 1983).

Wheat is currently the most important agricultural commodity in international markets and occupies about 20% of the world's farmed land (1977; Compendium of Wheat Diseases, Amer. Phytopath. Soc. page 1). Eightly percent of the world's supply of wheat is grown in North America, Europe, China, and the Soviet Union. Approximately 20% of the worldwide production of wheat is lost to disease annually.

Microdochium nivale (syns. Fusarium nivale and Gerlachia nivalis) is an important seed-borne pathogen of wheat (Hewett, 1983; Transactions of the British Mycological Society. Vol. 80:185–186). In a recent study in the UK, M. nivale was found in over 90% of the wheat seed samples tested (Reeves and Wray, 1984; British Crop Protection Council Monograph. Vol. 57:37–46). M. nivale also causes pink snow mold in wheat in the U.S., Canada, central Europe, and Scandinavia (1977; Compendium of Wheat Diseases, Amer. Phytopath. Soc. page 32). M. nivale and Fusarium spp. cause head blight (scab) in wheat spikes (1977; Compendium of Wheat Diseases, Amer. Phytopath. Soc. page 16). Significant yield losses may result from poor seed filling and floret sterility. M. nivale is also the predominate cause of foot rot disease in wheat (Pettitt, Parry and Polley, 1993; Mycological Research. Vol.97:1172–1174). Other important fungal pathogens involved in foot rot and head blight diseases include Fusarium species, such as F. culmorum, F. graminearum, and F. avenaceum (Schilling et al., 1996; Phytopathology Vol. 86, No. 5, pp. 515–522).

In view of the above, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides Internal Transcribed Spacer (ITS) DNA sequences that show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

In a preferred embodiment, the invention provides ITS 1 and ITS2 DNA sequences for the pathogens Fusarium poae, Fusarium avenaceum, and Microdochium nivale. In another preferred embodiment, the invention provides ITS-derived diagnostic primers for the detection of Fusarium spp. and Microdochium nivale.

This invention provides the possibility of assessing potential damage in a specific crop variety-pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase.

Kits useful in the practice of the invention are also provided. The kits find particular use in the identification of the fungal pathogens Fusarium spp. and Microdochium nivale.

DESCRIPTION OF THE FIGURE

FIG. 1 Sequence Alignment of the ITS regions from Fusarium culmorum, Fusarium graminearum, Fusarium poae, Microdochium nivale, and Fusarium moniliforme.

BRIEF DESCRIPTION OF THE SEQUENCES IN THE SEQUENCE LISTING

SEQ ID NO:1 Oligonucleotide Primer ITS1.
SEQ ID NO:2 Oligonucleotide Primer ITS2.

SEQ ID NO:3 Oligonucleotide Primer ITS3.
SEQ ID NO:4 Oligonucleotide Primer ITS4.
SEQ ID NO:5 M13 Universal-20 Primer.
SEQ ID NO:6 Reverse Primer used in Example 2.
SEQ ID NO:7 Oligonucleotide Primer JB605.
SEQ ID NO:8 Oligonucleotide Primer JB606.
SEQ ID NO:9 Oligonucleotide Primer JB607.
SEQ ID NO:10 Oligonucleotide Primer JB609.
SEQ ID NO:11 Oligonucleotide Primer JB610.
SEQ ID NO:12 Oligonucleotide Primer JB611.
SEQ ID NO:13 Oligonucleotide Primer JB612.
SEQ ID NO:14 Oligonucleotide Primer JB613.
SEQ ID NO:15 Oligonucleotide Primer JB614.
SEQ ID NO:16 Oligonucleotide Primer JB578.
SEQ ID NO:17 Oligonucleotide Primer JB571.
SEQ ID NO:18 Oligonucleotide Primer JB572.
SEQ ID NO:19 Consensus DNA sequence of the ITS region PCR-amplified from *Fusarium culmorum* isolates R-5106, R-5126 and R-5146, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:20 Consensus DNA sequence of the ITS region PCR-amplified from *Fusarium graminearum* isolates R-8417, R-8422 and R-8546, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:21 DNA sequence of the ITS region PCR-amplified from *Fusarium moniliforme* isolate 4551, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:22 Consensus DNA sequence of the ITS region PCR-amplified from *Fusarium poae* isolates T-427, T-534, and T-756, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:23 Consensus DNA sequence of the ITS region PCR-amplified from *Microdochium nivale* isolates 72, 520, and 18222, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.
SEQ ID NO:24 Consensus DNA sequence of the ITS region PCR-amplified from *Fusarium avenaceum* isolates 64452 and R-4045, comprising in the 5' to 3' direction: 3' end of the small subunit rRNA gene, Internal Transcribed Spacer 1, 5.8S rRNA gene, Internal Transcribed Spacer 2, and 5' end of the large subunit rRNA gene.

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene regions of particular fungal pathogens as well as primers derived from these regions that are capable of identifying the particular pathogen. These ITS DNA sequences from different pathotypes within a pathogen species or genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et aL, 1991; *Applied and Environ. Microbiol.* 57:553–556), and random amplified polymorphic DNA (i.e. RAPD) markers were able to distinguish numerous races of *Gremmeniella abietina,* the causal agent of scleroderris canker in conifers. U.S. Pat. No. 5,585,238 (herein incorporated by reference in its entirety) describes primers derived from the ITS sequences of the ribosomal RNA gene region of strains of *Septoria, Pseudocercosporella,* and *Mycosphaerella* and their use in the identification of these fungal isolates using PCR-based techniques. In addition, U.S. patent application Ser. No. 08/722,187 (herein incorporated by reference in its entirety) describes primers derived from the ITS sequences of the ribosomal RNA gene region of strains of *Fusarium* and their use in the identification of these fungal isolates using PCR-based techniques. Furthermore, U.S. patent application Ser. No. 08/742,023 (herein incorporated by reference in its entirety) describes primers derived from the ITS sequences of the ribosomal RNA gene region of strains of *Cercospora, Helminthosporium, Kabatiella,* and *Puccinia* and their use in the identification of these fungal isolates using PCR-based techniques.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al, 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Particular DNA sequences of interest include ITS DNA sequences from *Fusarium poae, Microdochium nivale,* and *Fusarium avenaceum.* Such ITS DNA sequences are disclosed in SEQ ID NOs:22–24, respectively. Sequences of representative oligonucleotide primers derived from these ITS sequences are disclosed in SEQ ID NOs:7–18. The sequences find use in the PCR-based identification of the pathotypes of interest.

Methods for the use of the primer sequences of the invention in PCR analysis are well known in the art. For example, see U.S. Pat. Nos. 4,683,195 and 4,683,202, as well as Schlesseretal. (1991) *Applied and Environ. Microbiol.* 57:553–556. See also, Nazar et al. (1991; *Physiol. and Molec. Plant Pathol.* 39:1–11), which used PCR amplification to exploit differences in the ITS regions of *Verticillium albo-atrum* and *Verticillium dahliae* and therefore distinguish between the two species; and Johanson and Jeger (1993; *MycoL Res.* 97:670–674), who used similar techniques to distinguish the banana pathogens *Mycosphaerella fijiensis* and *Mycospharella musicola*.

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287.

Alternatively, the ITS sequences of interest can be determined by PCR amplification. In an exemplified embodiment, primers to amplify the entire ITS region were designed according to White et al. (1990; In: PCR Protocols; Eds.: Innes et al. pages 315–322), and the amplified ITS sequence was subcloned into the pCRII cloning vector. The subcloned sequence included the left hand ITS (ITS1), the right hand ITS (ITS2), as well as the centrally located 5.8S rRNA gene. This was undertaken for several species of *Fusarium*, including *Fusarium poae* and *Fusarium avenaceum*, as well as *Microdochium nivale*.

The determined ITS sequences were compared within each pathogen group to locate divergences that might be useful to test in PCR to distinguish the different species and/or strains. The ITS DNA sequences that were determined are shown in SEQ ID NOs:19–24 and the comparative alignment is shown in FIG. 1. From the identification of divergences, numerous primers were synthesized and tested in PCR-amplification. Templates used for PCR-amplification testing were firstly purified pathogen DNA, and subsequently DNA isolated from infected host plant tissue. Thus, it was possible to identify pairs of primers that were diagnostic, i.e. that identified one particular pathogen species or strain but not another species or strain of the same pathogen. Primers were also designed to regions highly conserved among the species to develop genus-specific primers as well as primers that will identify any of several fungal pathogens that cause a particular disease. For example, primers were developed to detect *Fusarium* caused by various fungal pathogens, including *Fusarium* spp. and *Microdochium nivale*.

Preferred primer combinations are able to distinguish between the different species or strains in infected host tissue, i.e. host tissue that has previously been infected with a specific pathogen species or strain. This invention provides numerous primer combinations that fulfill this criterion for different *Fusarium* spp. and *Microdochium nivale*. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree °C. to achieve good sensitivity and should be void of significant secondary structure and 3' overlaps between primer combinations. Primers generally have sequence identity with at least about 5–10 contiguous nucleotide bases of ITS1 or ITS2. In preferred embodiments, primers are anywhere from approximately 5–30 nucleotide bases long.

The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the isolation of ITS sequences, the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual,* Cold Spring Harbor laboratory, Cold Spring Harbor, N.Y. (1989) and by T. J. Silhavy, M. L. Berman, and L. W. Enquist, *Experiments with Gene Fusions,* Cold Spring Harbor Laboratory, Cold Spring Harbor, N.Y. (1984) and by Ausubel, F. M. et al., *Current Protocols in Molecular Biology,* pub. by Greene Publishing Assoc. and Wiley-Interscience (1987).

Example 1

Fungal Isolates and Genomic Fungal DNA Extraction

See Table 1 for a listing of the fungal isolates used and their source. Fungi are grown in 150 ml potato dextrose broth inoculated with mycelial fragments from PDA (Potato Dextrose Agar) cultures. Cultures are incubated on an orbital shaker at 28° C. for 7–11 days. Mycelia are pelleted by centrifugation and then ground in liquid nitrogen, and total genomic DNA is extracted using the protocol of Lee and Taylor (1990; In: *PCR Protocols: A Guide to Methods and Applications;* Eds.: Innes et al.; pages 282–287).

TABLE 1

Source of Test Isolates

| Isolate | Organism | Orgin | Source |
|---|---|---|---|
| 69 | *Microdochium nivale* | — | Novartis-Basel[1] |
| 72 | *Microdochium nivale* | — | Novartis-Basel[1] |
| 92 | *Microdochium nivale* var. majus | — | Novartis-Basel[1] |
| 93 | *Microdochium nivale* var. majus | — | Novartis-Basel[1] |
| 520 | *Microdochium nivale* | — | Novartis-Basel[1] |
| 18222 | *Microdochium nivale* | Scotland | ATCC[2] |
| T-0427 | *Fusarium poae* | Lancaster County, PA USA | P. Nelson[3] |
| T-0534 | *Fusarium poae* | Rock Springs, PA USA | P. Nelson[3] |
| T-0756 | *Fusarium poae* | Unionville, PA USA | P. Nelson[3] |
| 36885 | *Fusarium graminearum* | Finland | ATCC[2] |
| R-8422 | *Fusarium graminearum* | Canada | P. Nelson[3] |
| R-8546 | *Fusarium graminearum* | Plevdiv, Bulgaria | P. Nelson[3] |
| R-8417 | *Fusarium graminearum* | Italy | P. Nelson[3] |
| R-9367 | *Fusarium graminearum* | Mercer County, PA, USA | P. Nelson[3] |
| R-9420 | *Fusarium graminearum* | Washington; USA | P. Nelson[3] |
| R-8637 | *Fusarium graminearum* | Settat, Morocco | P. Nelson[3] |
| 4551 | *Fusarium moniliforme* | Indiana, USA | L. Castor[4] |
| 13379 | *Fusarium roseum* | — | ATCC[2] |
| 64452 | *Fusarium avenaceum* | Poland | ATCC[2] |
| R-4045 | *Fusarium avenaceum* | Dubbo, Australia | P. Nelson[3] |
| R-4941 | *Fusarium avenaceum* | Southern Brazil | P. Nelson[3] |
| R-8547 | *Fusarium avenaceum* | Plevdiv, Bulgaria | P. Nelson[3] |
| R-6554 | *Fusarium avenaceum* | Pullman, Washington USA | P. Nelson[3] |
| 62215 | *Fusarium culmorum* | Switzerland | ATCC[2] |
| R-5391 | *Fusarium culmorum* | Germany | P. Nelson[3] |
| R-5126 | *Fusarium culmorum* | Minnesota, USA | P. Nelson[3] |
| R-7770 | *Fusarium culmorum* | Poland | P. Nelson[3] |
| R-5106 | *Fusarium culmorum* | Darling Downs, Australia | P. Nelson[3] |
| R-5146 | *Fusarium culmorum* | Finland | P. Nelson[3] |
| 44643 | *Pseudocercosporella herpotrichoides* - W type | Germany | ATCC[2] |
| 308 | *Pseudocercosporella herpotrichoides* - R type | — | Novartis-Basel[1] |
| 44234 | *Ceratobasidium cereale* | Netherlands | ATCC[2] |
| 11404 | *Drechslera sorokiniana* | Minnesota, USA | ATCC[2] |
| 60531 | *Cladosporium herbarum* | New Zealand | ATCC[2] |
| 38699 | *Septoria glycines* | Illinois, USA | ATCC[2] |
| 26517 | *Septoria tritici* | Minnesota, USA | ATCC[2] |
| 52476 | *Cercospora arachidicola* | Oklahoma, USA | ATCC[2] |
| 26380 | *Septoria avenae* f.sp. triticea | Minnesota, USA | P. Ueng[5] |
| 24425 | *Septoria nodorum* | Montana, USA | ATCC[2] |
| — | *Rhizoctonia solani* (salvia) | Vero Beach, Florida USA | Novartis-US[6] |

[1] Novartis Crop Protection Limited, Basel, Switzerland
[2] American Type Culture Collection, Rockville, Maryland, USA
[3] Dr. Paul Nelson, Penn State University, USA
[4] Dr. Loral Castor, Novartis Seeds Research, Bloomington, Illinois, USA
[5] Dr. Peter Ueng, USDA, Beltsville, Maryland, USA
[6] Novartis Crop Protection Inc., Research Triangle Park, NC, USA

Example 2

Isolation of the Internal Transcribed Spacer (ITS) Regions

Approximately 550-bp long internal transcribed spacer region fragments are PCR amplified from 10 ng of genomic DNA isolated from *F. graminearum* isolates R-8417, R-8422 and R-8546, *F. culmorum* isolates R-5106, R-5126 and R-5146, *F. moniliforne* isolate #4551, *F. poae* isolates T-0427, T-0534 and T-0756, *M. nivale* isolates 520, 72 and 18222, and *F. avenaceum* isolates 64452 and R-4045 using 50 pmol of primers ITS1 (5'TCCGTAGGTGAACCTGCGG-3'; SEQ ID NO:1) and ITS4 (5'-TCCTCCGCTTATTGATATGC-3';SEQ ID NO:4). PCRs are performed as described in Example 4. PCR products are purified using Promega's Wizard DNA Clean-up kit (Madison, Wis.). The DNA sequences of the ITS regions are determined by the dideoxy method using the Applied Biosystems (Foster City, Calif.) automated sequencer with the primers ITS1 (SEQ ID NO:1), ITS2 (5'-GCTGCGTTCTTCATCGATGC-3'; SEQ ID NO:2), ITS4 (SEQ ID NO:4) and the M13 universal -20 (5'-GTAAAACGACGGCCAGT-3'; SEQ ID NO:5) and Reverse (5'-AACAGCTATGACCATG-3'; SEQ ID NO:6) primers. The ITS primers ITS1, ITS2, ITS3, and ITS4 are detailed in White et aL (1990; In: PCR Protocols; Eds.: Innes et al. pages 315–322). PCR products from amplifications with *F. moniliforme* isolate #4551, *F. poae* isolates T-0427, T-0534 and T-0756 and *M. nivale* isolates 520, 72 and 18222 are cloned using the Invitrogen Corporation's (San Diego, Calif.) TA Cloning Kit (part no. K2000–01) using the PCR2.1 cloning vector.

Example 3

DNA Extraction from Wheat

DNA is extracted from wheat using a bulk maceration method. The bulk maceration method is used to isolate DNA from several naturally infected wheat heads or stems from the field to optimize the field sampling method for high throughput analysis.

Bulk Maceration Method (1) Place the appropriate number of wheat heads or stems in a Bioreba (Reinach, Switzerland) heavy duty plastic bag (cat#4901 00). Weigh the plant tissue, plastic bag with leaves minus the tare (weight of the plastic bag).

(2) Add an equal volume (ml) of Muller Extraction Buffer (0.1% w/v Tween-80; 0.04M Tris-Cl, pH 7.7; 0.15M NaCl; 0.1% w/v BSA-Pentex fraction V; 0.01% w/v sodium azide; 200 mM EDTA) per weight (g) of wheat tissue. Macerate the tissue using a Bioreba Homex 6 homogenizer set at 70. Grind the leaves until the tissue is fibrous.

(3) Pool the extracts from multiple bags, if used, and vortex well. Aliquote the extraction juice into eppendorf tubes on ice.

(a) Boil 100 µl of the concentrated extract for 5 minutes.

(b) Place the boiled extract on ice.

(c) Make a 1:10 dilution by adding 10 µl from the boiled, concentrated extract to 90 µl of sterile dH$_2$O.

(d) Store the diluted extracts on ice until ready to use.

Example 4

Polymerase Chain Reaction Amplification

Polymerase chain reactions are performed with the Gene-Amp Kit from Perkin-Elmer/Cetus (Norwalk, Conn.; part no. N808-0009) using 50 mM KCl, 2.5 mM MgCl$_2$, 10 mM Tris-HCl, pH8.3, containing 200 µM of each dTTP, dATP, dCTP, and dGTP, 50 pmol each primer, 2.5 units of Taq polymerase and 10 ng of genomic DNA or 1 µl of 1:10 diluted plant extract in a final volume of 50 µl. Reactions are run for 30–40 cycles of 15 s at 94° C., 15 s at 50° C.–70° C., and 45 s at 72° C. in a Perkin-Elmer/Cetus Model 9600 thermal cycler. The products are analyzed by loading 10 µl of each PCR sample on a 1.0% agarose gel and electrophoresing.

Example 5

Synthesis and Purification of Oligonucleotides

Oligonucleotides (primers) are synthesized by, for example, either Integrated DNA Technologies (Coralville, Iowa) or Midland Certified Reagent Company (Midland, Tex.).

Example 6

Selection of Species-Specific Primers

FIG. 1 shows an alignment of the sequences of the ITS regions of *F. culmorum, F. graminearum, F. poae, M. nivale,* and *F. moniliforme.* Oligonucleotide primers such as those shown below in Table 2 are synthesized according to Example 5 based on analysis of the aligned sequences. Primers are designed to the regions that contain the greatest differences in sequence among the fungal species. Primers are also designed to regions highly conserved among the species in attempt to develop genus-specific primers. In addition, the published ribosomal gene-specific primers ITS1, ITS2, ITS3 and ITS4 (White et al., 1990; In: PCR Protocols; Eds.: Innes et al. pages 315–322) are synthesized for testing in combination with the primers specific for the ITS regions. Primers targeted to *Fusarium* spp. from WO 95/29260 are also used in combination with the newly designed primers to test for novel specificities.

TABLE 2

Primers Designed for Fungal Detection

| Primer Template | Primer | Primer Sequence |
| --- | --- | --- |
| Fusarium spp.[1] | JB605 | 5'CCAAACCATGTGAACTTACC3' (SEQ D NO: 7) |
| M. nivale | JB606 | 5'GGACTACCTAAACTCTGTT3' (SEQ ID NO: 8) |
| M. nivale | JB607 | 5'AGGGATCATTACCGAGTTT3' (SEQ ID NO: 9) |
| M. nivale | JB609 | 5'TCCGGCTTGCAGAAGCGAG3' (SEQ ID NO: 10) |
| M. nivale | JB610 | 5'GAAGGGTGCGGTTTATGGCT3' (SEQ ID NO: 11) |
| M. nivale | JB611 | 5'GCCACCGCCGGTGGAC3' (SEQ ID NO: 12) |
| M. nivale | JB612 | 5'GGTGCTGTCTCTCGGGAC3' (SEQ ID NO: 13) |
| M. nivale | JB613 | 5'AGTCAATCTGAATCAAACTAAG3' (SEQ ID NO: 14) |
| M. nivale | JB614 | 5'CTAAACTCTGTTAATTTTTGTCAA3' (SEQ ID NO: 15) |
| Fusarium spp.[2] | JB578 | 5'CCGCGACGATTACCAG3' (SEQ ID NO: 16) |
| F. gram. + F. culm.[3] | JB571 | 5'TAACGATATGTAAATTACTACGCT3' (SEQ ID NO: 17) |
| F. gram. + F. culm.[3] | JB572 | 5'AAGTTGGGGTTTAACGGC3' (SEQ ID NO: 18) |
| 18S rDNA | ITS1 | 5'TCCGTAGGTGAACCTGCGG3' (SEQ ID NO: 1) |
| 5.8S rDNA | ITS2 | 5'GCTGCGTTCTTCATCGATGC3' (SEQ ID NO: 2) |
| 5.8S rDNA | ITS3 | 5'GCATCGATGAAGAACGCAGC3' (SEQ ID NO: 3) |
| 25S rDNA | ITS4 | 5'TCCTCCGCTTATTGATATGC3' (SEQ ID NO: 4) |

[1]Fusarium spp. includes *F. graminearum, F. culmorum, F. avenaceum, F. poae* and *F. moniliforme.*
[2]Fusarium spp. includes *F. graminearum, F. culmorum, F. poae, F. moniliforme* and *F. roseum.*
[3]Primer combination only tested against *F. graminearum, F. culmorum* and *M. nivale.*

Example 7

Determination of Primer Specificity to Purified Fungal Genomic DNA

PCRs are performed according to Example 4 using different primer combinations (Table 3) in an attempt to amplify a single specific fragment. Specific PCR amplification products are produced from primers designed from the ITS regions between the 18S and 25S ribosomal DNA subunits of each fungal strain of interest.

TABLE 3

ITS-Derived Diagnostic PCR Primers

| Primer Specificity | 5'Primer | 3'Primer | Approximate size of amplified fragment |
|---|---|---|---|
| M. nivale | JB612 (SEQ ID NO:13) | IT54 (SEQ ID NO:4) | 472 bp |
| M. nivale | JB613 (SEQ ID NO:14) | JB610 (SEQ ID NO:11) | 337 bp |
| M. nivale | JB614 (SEQ ID NO:15) | JB610 (SEQ ID NO:11) | 355 bp |
| M. nivale | JB613 (SEQ ID NO:14) | ITS4 (SEQ ID NO:4) | 413 bp |
| M. nivale | JB614 (SEQ ID NO:15) | 1T54 (SEQ ID NO:4) | 431 bp |
| M. nivale | JB611 (SEQ ID NO:12) | JB609 (SEQ ID NO:10) | 346 bp |
| M. nivale | JB611 (SEQ ID NO:12) | ITS4 (SEQ ID NO:4) | 450 bp |
| M. nivale | ITS1 (SEQ ID NO:1) | JB609 (SEQ ID NO:10) | 452 bp |
| M. nivale | ITS1 (SEQ ID NO:1) | JB610 (SEQ ID NO:11) | 480 bp |
| M. nivale | JB605 (SEQ ID NO:7) | JB610 (SEQ ID NO:11) | 433 bp |
| M. nivale | JB606 (SEQ ID NO:8) | JB610 (SEQ ID NO:11) | 362 bp |
| M. nivale | JB607 (SEQ ID NO:9) | JB610 (SEQ ID NO:11) | 460 bp |
| Fusarium spp.[1] + M. niv | JB605 (SEQ ID NO:7) | IT54 (SEQ ID NO:4) | 509 bp |
| Fusarium spp.[2] | JB605 (SEQ ID NO:7) | JB578 (SEQ ID NO:16) | 417 bp |
| F. gram. + F. culm.[3] | JB605 (SEQ ID NO:7) | JB572 (SEQ ID NO:18) | 440 bp |
| F. gram. + F. culm.[3] | JB605 (SEQ ID NO:7) | JB571 (SEQ ID NO:17) | 400 bp |

[1]Fusarium spp. includes F. graminearum, F. culmorum, F. avenaceum, F. poae and F. moniliforme.
[2]Fusarium spp. includes F. graminearum, F. culmorum, F. poae, F. moniliforme and F. roseum.
[3]Primer combination only tested against F. graminearum, F. culmorum and M. nivale.

Example 8

Determination of Primer Specificity to Plant Tissue Infected with Fungi and Cross-Reactivity with Other Cereal Fungal Pathogens Total genomic DNA is isolated as described in Example 3 from healthy wheat heads and from wheat heads inoculated with M. nivale, F: graminearum, F. culmorum, or F. avenaceum. PCRs are performed as described in Example 4 testing primer combinations such as those listed in Table 3 against DNA from the wheat tissue. Purified fungal genomic DNAs are obtained as described in Example 1 and PCR assayed as described in Example 4 using the diagnostic primers. Other fungal DNA species and isolates are tested for the ability of the diagnostic primers to cross-react therewith. The results of representative experiments are as follows:

M. nivale-specific primer combination JB612 (SEQ ID NO:13) and ITS4 (SEQ ID NO:4) amplified a 472 bp fragment from DNA from all of the M. nivale isolates listed in Table 1 and from M. nivale-infected wheat tissue. This primer combination did not amplify a diagnostic fragment from healthy wheat tissue nor from purified genomic DNA from F. graminearum, F. culmorum, F. avenaceum, F. poae or F. moniliforme. This primer combination also did not amplify a diagnostic fragment from purified genomic DNA isolated from the following common cereal pathogens: P. herpotrichoides R- and W-pathotypes, C. cereale, D. sorokiniana, C. herbarum, S. glycines, S. tritici, C. arachidicola, S. nodorum, R. solani and S. avenae f.sp. triticea. Similar diagnostic results were obtained with M. nivale-specific primer combination JB613 (SEQ ID NO:14) and JB610 (SEQ ID NO:11).

Primer combination JB613 (SEQ ID NO:14) and ITS4 (SEQ ID NO:4) amplified a 413 bp fragment, and primer combination JB614 (SEQ ID NO:15) and ITS4 (SEQ ID NO:4) amplified a 431 bp fragment from DNA from M. nivale isolate #520 and from wheat infected with M. nivale. These primer combinations did not amplify any fragments from healthy wheat tissue, nor from DNA from F. graminearum isolate #R-8422 and F. culmorum isolate #R-5391.

The remaining M. nivale-specific primer combinations listed in Table 3 amplified a PCR fragment from DNA from M. nivale isolate #520 but not from DNA from F. graminearum isolate #R-8422 nor F. culmorum isolate #R-5391.

Primer combination JB605 (SEQ ID NO:7) and ITS4 (SEQ ID NO:4) amplified a 509 bp fragment from DNA from all of the M. nivale isolates listed in Table 1. This primer combination also amplified a 509 bp fragment from DNA from all of the F. graminearum, F. culmorum, F. avenaceum, F. poae and F. moniliforme isolates listed in Table 1. This primer combination did not amplify a diagnostic fragment from purified genomic DNA isolated from the following cereal pathogens: P. herpotrichoides R- and W-pathotypes, C. cereale, D. sorokiniana, C. herbarum, S. glycines, S. tritici, C. arachidicola, S. nodorum, R. solani and S. avenae f.sp. triticea. Primer combination JB605 (SEQ ID NO:7) and ITS4 (SEQ ID NO:4) also amplified a diagnostic fragment from wheat infected with Fusarium spp. but not from healthy wheat.

Primer combinations JB605 (SEQ ID NO:7) and JB571 (SEQ ID NO:17), JB605 (SEQ ID NO:7) and JB572 (SEQ ID NO:18), and JB605 (SEQ ID NO:7) and JB578 (SEQ ID NO:16) amplified 400 bp, 440 bp and 417 bp fragments, respectively, from DNA from F. graminearum isolate #R-8422 and F. culmorum isolate #R-5391, but not from M. nivale isolate #520. In addition, primer combination JB605 (SEQ ID NO:7) and JB578 (SEQ ID NO:16) amplified a diagnostic fragment from all of the F. graminearum, F. moniliforme, F. roseum, F. poae and F. culmorum isolates listed in Table 1; however, this primer combination did not amplify from any of the F. avenaceum isolates nor M. nivale isolates listed in Table 1. Primer combinations JB605 (SEQ ID NO:7) and JB571 (SEQ ID NO:17), JB605 (SEQ ID NO:7) and JB572 (SEQ ID NO:18), and JB605 (SEQ ID NO:7) and JB578 (SEQ ID NO:16) did not amplify a diagnostic fragment from healthy wheat or from purified genomic DNA isolated from the cereal pathogens P. herpotrichoides R- and W-pathotypes, C. cereale, D. sorokiniana, C. herbarum, S. glycines, S. tritici, C. arachidicola, S. nodorum, R. solani and S. avenae f.sp. triticea.

While the present invention has been described with reference to specific embodiments thereof, it will be appre-

What is claimed is:

1. An isolated Internal Transcribed Spacer sequence selected from the group consisting of: ITS1 of *Fusarium poae* comprising nucleotides 31–180 of SEQ ID NO:22, ITS2 *of Fusarium poae* comprising nucleotides 338–489 of SEQ ID NO:22, ITS1 of*Microdochium nivale* comprising nucleotides 31–175 of SEQ ID NO:23, ITS2 of *Microdochium nivale* comprising nucleotides 333–499 of SEQ ID NO:23, ITS1 of *Fusarium avenaceum* comprising nucleotides 31–181 of SEQ ID NO:24, and ITS2 of *Fusarium avenaceum* comprising nucleotides 339–504 of SEQ ID NO:24.

2. An oligonucleotide primer for use in identification of a fungal pathogen, wherein said oligonucleotide primer is selected from the group consisting of SEQ ID NO's:7–15.

3. A pair of oligonucleotide primers for use in the amplification-based detection of a fungal Internal Transcribed Spacer DNA sequence, wherein at least one of said primers is the oligonucleotide primer of claim 2.

4. A pair of oligonucleotide primers according to claim 3, wherein said pair is selected from the following primer pairs:

SEQ ID NO:13 and SEQ ID NO:4;
SEQ ID NO:14 and SEQ ID NO:11;
SEQ ID NO:15 and SEQ ID NO:11;
SEQ ID NO:14 and SEQ ID NO:4;
SEQ ID NO:15 and SEQ ID NO:4;
SEQ ID NO:12 and SEQ ID NO:10;
SEQ ID NO:12 and SEQ ID NO:4;
SEQ ID NO:1 and SEQ ID NO:10;
SEQ ID NO:1 and SEQ ID NO:11;
SEQ ID NO:7 and SEQ ID NO:11;
SEQ ID NO:8 and SEQ ID NO:11;
SEQ ID NO:9 and SEQ ID NO:11;
SEQ ID NO:7 and SEQ ID NO:4;
SEQ ID NO:7 and SEQ ID NO:16;
SEQ ID NO:7 and SEQ ID NO:18; and
SEQ ID NO:7 and SEQ ID NO:17.

5. A pair of oligonucleotide primers according to claim 4, wherein said pair of primers is used to detect *Microdochium nivale,* and wherein said pair is selected from the following primer pairs:

SEQ ID NO:13 and SEQ ID NO:4;

SEQ ID NO:14 and SEQ ID NO:11;
SEQ ID NO:15 and SEQ ID NO:11;
SEQ ID NO:14 and SEQ ID NO:4;
SEQ ID NO:15 and SEQ ID NO:4;
SEQ ID NO:12 and SEQ ID NO:10;
SEQ ID NO:12 and SEQ ID NO:4;
SEQ ID NO:1 and SEQ ID NO:10;
SEQ ID NO:1 and SEQ ID NO:11;
SEQ ID NO:7 and SEQ ID NO:11;
SEQ ID NO:8 and SEQ ID NO:11; and
SEQ ID NO:9 and SEQ ID NO:11.

6. A pair of oligonucleotide primers according to claim 4, wherein said pair of primers is used to detect *Microdochium nivale, F. graminearum, F. culmorum, F. avenaceum, F. poae,* and *F. moniliforme,* and wherein said pair is SEQ ID NO:7 and SEQ ID NO:4.

7. A pair of oligonucleotide primers according to claim 4, wherein said pair of primers is used to detect *F. graminearum, F. moniliforme, F. roseum, F. poae,* and *F. culmorum* and wherein said pair is SEQ ID NO:7 and SEQ ID NO:16.

8. A pair of oligonucleotide primers according to claim 4, wherein said pair of primers is used to detect *F. graminearum* and *F. culmorum,* and wherein said pair is selected from the following primer pairs:
SEQ ID NO:7 and SEQ ID NO:18; and
SEQ ID NO:7 and SEQ ID NO:17.

9. A method for the detection of a fungal pathogen selected from the group consisting of *Fusarium poae, Microdochium nivale,* and *Fusarium avenaceum,* comprising the steps of:
  (a) isolating DNA from a plant leaf infected with said pathogen;
  (b) subjecting said DNA to polymerase chain reaction amplification using at least one primer having sequence identity with at least 10 contiguous nucleotides of a sequence selected from the group consisting of: nucleotides 31–180 of SEQ ID NO:22, nucleotides 338–489 of SEQ ID NO:22, nucleotides 31–175 of SEQ ID NO:23, nucleotides 333–499 of SEQ ID NO:23, and nucleotides 339–504 of SEQ ID NO:24; and
  (c) detecting said fungal pathogen by visualizing the product or products of said polymerase chain reaction amplification.

10. The method of claim 9, wherein said fungal pathogen is *Fusarium poae.*

11. The method of claim 9, wherein said fungal pathogen is *Microdochium nivale.*

12. The method of claim 9, wherein said fungal pathogen is *Fusarium avenaceum.*

13. An isolated Internal Transcribed Spacer sequence according to claim 1, wherein said Internal Transcribed Spacer sequence is selected from the group consisting of: ITS1 and ITS2 of *Fusarium poae.*

14. An isolated Internal Transcribed Spacer sequence according to claim 1, wherein said Internal Transcribed Spacer sequence is selected from the group consisting of: ITS1 and ITS2 of *Microdochium nivale.*

15. An isolated Internal Transcribed Spacer sequence according to claim 1, wherein said Internal Transcribed Spacer sequence is selected from the group consisting of: ITS1 and ITS2 of *Fusarium avenaceum.*

16. The method of claim 10, wherein said primer has sequence identity with at least 10 contiguous nucleotides of nucleotides 31–180 of SEQ ID NO:22.

17. The method of claim 10, wherein said primer has sequence identity with at least 10 contiguous nucleotides of nucleotides 338–489 of SEQ ID NO:22.

18. The method of claim 11, wherein said primer has sequence identity with at least 10 contiguous nucleotides of nucleotides 31–175 of SEQ ID NO:23.

19. The method of claim 11, wherein said primer has sequence identity with at least 10 contiguous nucleotides of nucleotides 333–499 of SEQ ID NO:23.

20. The method of claim 12, wherein said primer has sequence identity with at least10 contiguous nucleotides of nucleotides 339–504 of SEQ ID NO:24.

21. A method for the detection of *Fusarium avenaceum,* comprising the steps of:
  (a) isolating DNA from a plant leaf infected with *Fusarium avenaceum;*
  (b) subjecting said DNA to polymerase chain reaction amplification using at least one primer having sequence identity with at least 10 contiguous nucleotides of nucleotides 31–118 or 138–181 of SEQ ID NO:24; and
  (c) detecting *Fusarium avenaceum* by visualizing the product or products of said polymerase chain reaction amplification.

* * * * *